(12) United States Patent
Von Drasek et al.

(10) Patent No.: US 6,859,766 B2
(45) Date of Patent: Feb. 22, 2005

(54) INDIRECT GAS SPECIES MONITORING USING TUNABLE DIODE LASERS

(75) Inventors: William A. Von Drasek, Oak Forest, IL (US); Victor M. Saucedo, Willowbrook, IL (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 10/364,675

(22) Filed: Feb. 11, 2003

(65) Prior Publication Data

US 2003/0233212 A1 Dec. 18, 2003

Related U.S. Application Data

(60) Provisional application No. 60/356,107, filed on Feb. 11, 2002.

(51) Int. Cl.[7] .............................................. F23N 5/08
(52) U.S. Cl. .................... 702/194; 702/30; 702/31; 702/32; 431/79
(58) Field of Search ........................ 702/194, 30–32; 431/1, 2, 5, 12, 13, 25, 75, 76, 79

(56) References Cited

U.S. PATENT DOCUMENTS

| | | | | |
|---|---|---|---|---|
| 3,920,447 A | * | 11/1975 | Schroeder et al. .............. 75/530 |
| 3,970,955 A | * | 7/1976 | Lee .............................. 372/89 |
| 4,745,070 A | * | 5/1988 | Korcek et al. ................. 436/60 |
| 4,896,965 A | * | 1/1990 | Goff et al. .................... 356/417 |
| 4,913,647 A | * | 4/1990 | Bonne et al. .................. 431/12 |
| 5,311,421 A | * | 5/1994 | Nomura et al. ................. 70/37 |
| 5,333,487 A | * | 8/1994 | Kimura et al. ............... 73/23.31 |
| 5,369,241 A | * | 11/1994 | Taylor et al. ............. 219/121.49 |
| 5,486,675 A | * | 1/1996 | Taylor et al. ............. 219/121.59 |
| 5,686,988 A | * | 11/1997 | Garrett ........................ 356/318 |
| 5,750,992 A | * | 5/1998 | Van Pelt et al. .............. 250/372 |
| 6,045,353 A | * | 4/2000 | VonDrasek et al. ............ 431/79 |
| 6,301,572 B1 | * | 10/2001 | Harrison ........................ 706/52 |
| 6,372,009 B1 | * | 4/2002 | Holmes et al. ............... 75/10.36 |
| 2001/0014436 A1 | * | 8/2001 | Lemelson et al. ............. 431/12 |
| 2002/0158202 A1 | * | 10/2002 | Webber et al. ............. 250/339.13 |
| 2003/0093246 A1 | * | 5/2003 | Daw et al. .................... 702/188 |

OTHER PUBLICATIONS

Gregory, *Results of ALARC–PCTM Post Combustion at Cascade Steel Rolling Mills, Inc.*, 1995 Electric Arc Furnace Conference Proceedings, p. 211–217.

Jones, et al., *Post–Combustion, A Practical and Technical Evaluation*, 1995 Electric Arc Furnace Conference Proceedings, p. 199–210.

Grant, et al., *Efficiency of Oxygen Technologies in EAF*, The AISE Steel Foundation 200 Proceedings, Pittsburgh, PA (2000).

Dietrich, et al., *Laser Analysis of CO and Oxygen in EAF Off–Gas*, 59th Electric Furnance Conference and 19th Proceedings, Iron and Steel Society (2001).

Okabe, *Photo–Chemistry of Small Molecules*, John Wiley & Sons, New York, p. 166 (1978).

\* cited by examiner

*Primary Examiner*—Carol S W Tsai
(74) *Attorney, Agent, or Firm*—Linda K. Russell; Christopher J. Cronin

(57) ABSTRACT

A method for indirect gas species monitoring based on measurements of selected gas species is disclosed. In situ absorption measurements of combustion species are used for process control and optimization. The gas species accessible by near or mid-IR techniques are limited to species that absorb in this spectral region. The absorption strength is selected to be strong enough for the required sensitivity and is selected to be isolated from neighboring absorption transitions. By coupling the gas measurement with a software sensor gas, species not accessible from the near or mid-IR absorption measurement can be predicted.

12 Claims, 4 Drawing Sheets

INDIRECT GAS SPECIES MONITORING USING TUNABLE DIODE LASERS

CROSS REFERENCE TO RELATED APPLICATION

This application claims the benefit of U.S. Provisional Application Ser. No. 60/356,107, filed Feb. 11, 2002.

BACKGROUND OF THE INVENTION

1. Field of the Invention

A method for indirect gas species monitoring based on measurements of selected gas species is disclosed. Application of in situ absorption measurements of key combustion species, such as $O_2$, CO, $CO_2$ and $H_2O$, can be used for process control and optimization. In situ absorption measurements offer a number of advantages over conventional extractive sampling in terms of maintenance and response time. However, the gas species accessible by near or mid-IR techniques are limited to species that absorb in this spectral region. Additionally, the absorption strength must be strong enough for the required sensitivity and isolated from neighboring absorption transitions. By coupling the gas measurement with a software sensor gas, species not accessible from the near or mid-IR absorption measurement can be predicted.

2. Description of Prior Art

It has long been recognized that knowledge of the exhaust gas composition from a process can be used in process optimization through control algorithms. Improvements in energy efficiency, pollutant minimization, and production increase and/or quality control are some of the benefits experienced by coupling gas composition measurements to a control system. For example, in the manufacturing of secondary steel, electric arc furnaces are used to melt the scrap metal. These processes operate in a batch mode, by filling the vessel with scrap and then introducing an AC or DC electrode to form a high temperature plasma, as an energy source to melt the scrap. In addition, assist burners are used to transfer additional chemical heat to the process. Quality control of the melt is conducted by extracting molten samples from the bath to test for the desired carbon content.

During this melt process the exhaust gas released from the vessel can contain high concentrations of CO and $H_2$, greater than about forty percent, as a result of incomplete combustion of $O_2$ and fuel in the furnace. Sources of CO and $H_2$ can be traced to scrap mix characteristics that can contain oils, paints, and other hydrocarbon-based material. At different phases of the melt process, the levels of CO and $H_2$ can vary dramatically, due to the random nature of the scrap trapping and to the release of gas in puffs when sections of the melt collapse. The release of these combustible gases can represent more than about thirty percent of the furnace off-gas, resulting in a tremendous loss of chemical energy.

Recovering energy available in the EAF exhaust gas has been demonstrated by conducting post-combustion of the off-gas with $O_2$ injection. Gregory, RESULTS OF ALARC-PCTM POST-COMBUSTION AT CASCADE STEEL ROLLING MILLS, INC., 1995 Electric Arc Furnace Conference Proceedings, p. 211–217 (1995); Jones, et al., POST-COMBUSTION, A PRACTICAL AND TECHNICAL EVALUATION, 1995 Electric Arc Furnace Conference Proceedings, p. 199–210(1995) and Grant, et al., EFFICIENCY OF OXYGEN TECHNOLOGIES IN THE EAF, The AISE Steel Foundation 200 Proceedings, Pittsburgh, Pa. (2000). In these examples, the amount of $O_2$ injected was monitored by knowing the off-gas composition, to prevent overloading or underloading the furnace with $O_2$. Additionally, the off-gas composition was monitored with conventional extractive sampling techniques. This is currently the accepted practice, not only on EAF processes, but also on the majority of combustion processes.

Off-gas analysis from a combustion process can be performed using an extractive sampling probe that is typically water-cooled and inserted into the process. The sequence of events in extractive gas sampling are as follows: 1) a gas sample is pulled through the probe inserted into the process quenching the reaction mixture; 2) passed through a chiller for water removal; 3) passed through a filter for particle removal; 4) compressed by the sampling pump; 5) directed through an analyzer or series of analyzers to measuring dry gas concentration. The analyzer used typically consists of one of the following types: a gas chromatograph, mass spectrometer, nondispersive infrared or dispersive infrared. Gas chromatographs perform a batch analysis, and therefore have the slowest response time from the techniques list. Mass spectrometers provide continuous monitoring with fast-response times, but are sensitive to dirty gases and steams. Moreover, interpretation of the mass spectra is complicated by overlapping mass fragments. This is most evident when interpreting spectra containing CO and $N_2$ species, since both have the same atomic mass unit. For these reasons either dispersive or nondispersive IR analyzers are generally used.

For off-gas analysis of combustion processes, the key species typically monitored are $O_2$, CO, $CO_2$ and $H_2$. Generally, $H_2O$ is not monitored, since the volume is high from the combustion process; only the dry gas is analyzed. In the case of EAF off-gas analyses, CO and $CO_2$ are monitored with NDIR instruments, $O_2$ detection is by either resonance paramagnetic or electrolytic cells, and solid-state analyzers are used for $H_2$ detection.

Though extractive sampling has a long history and is an accepted practice for many combustion applications, disadvantages such as slow response time, susceptibility to probe plugging and corrosion, and being a single point measurement, hamper acceptance of this approach as a continuous routine means for process monitoring. In particular, on processes with high levels of particulate matter, such as the EAF, waste incineration, and gasification, maintaining a sampling probe becomes difficult. To avoid these problems, alternatives to extractive sampling are emerging using non-intrusive optical techniques.

A number of in situ demonstration measurements using optical techniques such as diode lasers have been conducted on harsh combustion processes. In this case, a diode laser is tuned at the frequency of an absorption transition of the molecule of interest. A number of examples in the literature demonstrate the use of diode lasers to monitor the exhaust gas from a process. For example, Sandia National Laboratory demonstrated analysis of the off-gas using diode lasers operating in the mid-JR, working with the American Iron and Steel Institute. In their patent WO 99/26058, they disclose using a diode laser propagating through the gap between the furnace exhaust and the main exhaust to measure CO, $CO_2$ and $H_2O$.

Near-IR monitoring of CO and $O_2$ on an EAF has been discussed by Dietrich, et al., LASER ANALYSIS OF CO AND OXYGEN IN EAF OFF-GAS, $59^{th}$ Electric Furnace Conference and $19^{th}$ Process Technology Conference Proceedings, Iron and Steel Society (2001). In this case, water-cooled pipes are used on each side of the furnace gap to launch and receive the beam. The optical techniques demonstrated are not only non-intrusive, but also provide real-time information on the gas composition eliminating any issues related to measurement delay times. However, in the case of an EAF process where significant levels of $H_2$ are present, an in situ optical absorption measurement is not feasible, since absorption transitions for $H_2$ occurs in the Lyman bands between 850 and 1108 Å (Okabe, Photo-Chemistry of Small Molecules, John Wiley & Sons, New York, page 166 (1978)), which is in the vacuum ultraviolet spectral region.

Hence, no reliable, accurate and real-time method is currently available for monitoring off-gas species concentrations in high-temperature, high-particulate combustion processes, such as in electric arc furnaces, which has prevented so far the dynamic control of such processes and the optimization of their efficiency.

Thus, a problem associated with methods for sampling and continuously monitoring off-gases from an industrial furnace that precede the present invention is that they provide a slow response time and thereby do not adequately indicate process conditions to enable optimal process control.

A further problem associated with methods for sampling and continuously monitoring off-gases from an industrial furnace that precede the present invention is that they do not provide point measurements, and therefore do not allow sampling the off-gas specifically in the desired locations of the exhaust stream.

Yet another problem associated with methods for monitoring the off-gases of an industrial combustion process that precede the present invention is that they are susceptible to probe plugging and corrosion.

An even further problem associated with methods for monitoring the off-gases of an industrial combustion process that precede the present invention is that they require undue replacement of the monitoring equipment.

Still a further problem associated with methods for monitoring the off-gases of an industrial combustion process that precede the present invention is that they do not provide continuous, near real-time measurements of the species concentration in the waste gases, with acceptable accuracy, so as to facilitate an adapted dynamic monitoring of process characteristics.

In contrast to the foregoing, the present invention provides a method for indirect monitoring that uses tunable diode lasers that seeks to overcome the foregoing problems and provide a more simplistic, more easily constructed and relatively reliable methodology.

For the foregoing reasons, there has been defined a long felt and unsolved need for a method for indirect monitoring that uses tunable diode lasers that seeks to overcome the problems discussed above, while at the same time providing a simple, easily constructed and maintained design that facilitates more reliable process control.

SUMMARY OF THE INVENTION

A method for indirectly monitoring the $H_2$ concentration using the measured values of CO, $CO_2$ and $H_2O$ obtained by either mid-IR or near-IR absorption measurements is disclosed. Inclusion of $H_2$ monitoring into the set of species provides an accurate measure of the combustion gas reducing state that can be adjusted with the controlled amount of $O_2$ injection. In addition, improved mass and energy audits are obtained by having real-time data regarding the gas composition and temperature.

Thus, an object of the present invention is to provide a method for indirect monitoring that uses tunable diode lasers for sampling and continuously monitoring off-gases from an industrial furnace that has a more immediate response time and thereby indicates process conditions more quickly, to enable optimal process control.

A further object of the present invention is to provide a method for indirect monitoring that uses tunable diode lasers that provides point measurements, allowing sampling the off-gas specifically in the desired locations of the exhaust stream.

Yet another object of the present invention is to provide a method for indirect monitoring that uses tunable diode lasers that is not susceptible to probe plugging and corrosion.

An even further object of the present invention is to provide a method for indirect monitoring that uses tunable diode lasers that does not require undue replacement of the monitoring equipment.

Yet another object of the present invention is to provide a method for indirect monitoring that uses tunable diode lasers that provides continuous, near real-time measurements of the species concentration in the waste gases, with acceptable accuracy, so as to facilitate an adapted dynamic monitoring of process characteristics.

These and other objects, advantages and features of the present invention will be apparent from the detailed description that follows.

BRIEF DESCRIPTION OF THE DRAWINGS

In the detailed description that follows, reference will be made to the following figures.

DETAILED DESCRIPTION OF A PREFERRED EMBODIMENT

Figure 1:
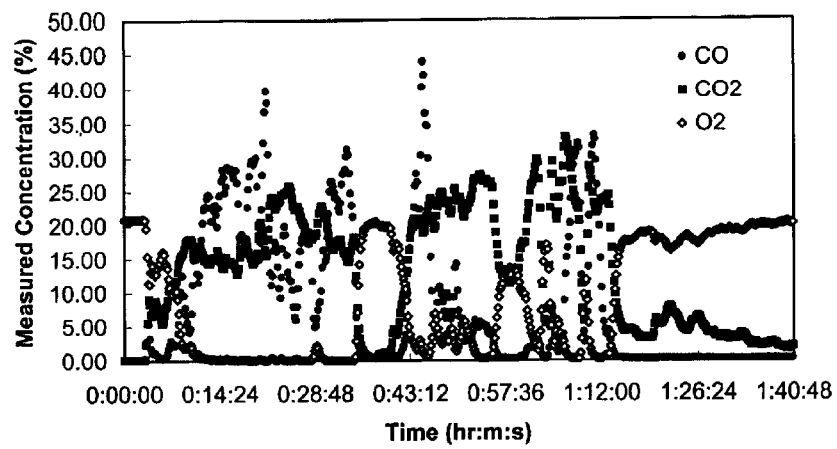
FIG. 1 shows data for the measured concentration of CO, $CO_2$ and $O_2$ as a function of time.

For harsh combustion monitoring where particulate matter and/or a corrosive atmosphere are present, extractive sampling probes are not readily maintained. The preferred method is to use an in situ optical measurement that is not susceptible to issues related to particulate matter or the gas atmosphere because the measurement is non-intrusive. However, optical techniques are limited by the accessible wavelength range, putting a restriction on detection of certain species. For industrial applications, the system must be robust enough to survive the surrounding environment. Diode lasers satisfy this requirement since they are compact, solid-state devices that, in the near-IR, can be fiber optically coupled, which allows transporting the light to the process by fiber optics while the more sensitive electronics are placed in a controlled environment, e.g., a furnace operator control room.

Typically, $H_2$ absorption measurements are not possible using near or mid-IR lasers. Therefore, to obtain information on the level of $H_2$ concentration present, a software sensor based on neural network (NN) algorithms can be used to predict the $H_2$ concentration based on near or mid-JR absorption measurements of CO, $CO_2$, and $H_2O$. In this application, the measured values would be direct to a software sensor-processing unit to then predict the level of $H_2$ present.

Prior to using the software-sensor, the NN requires training by some means to measure $H_2$. Here, conventional extractive sampling can be used for a short period to collect sufficient process data for training. Once the software-sensor is trained, the extractive system is no longer needed, and measurements using only the optical absorption technique can be carried out.

Additionally, a software-sensor approach facilitates indirect monitoring of $H_2$. A combination of multi-species monitoring by absorption and a software-sensor prediction of other species is performed. For example, NO pollutant from the exhaust of combustion processes is of interest for environmental reasons. However, in situ, near-IR diode laser measurements of NO have not been possible on industrial processes because the absorption linestrength is weak and the spectral region is extremely congested with surrounding $H_2O$ lines. For these reasons, examples of NO combustion monitoring are extractive sampling and gas conditioning, i.e., removing $H_2O$ prior to conducting the measurement in a multi-pass cell to increase the measurement pathlength.

However, there is a strong correlation between the level of NO and the amount of excess $O_2$ which is related to the Zeldovich mechanism. Combustion exhaust streams that experience an increase in the level of excess $O_2$ also show an increase in the NO concentration level. In this application, a diode laser system can measure $O^2$, $CO_2$ and $H_2O$ concentration, in addition to gas temperature, as input into the software sensor to predict the NO concentration. As before, the NN must first be trained with measured NO concentrations from another method, such as extractive sampling.

On-line measurement allows performing several advanced calculations, such as feedback control and real-time optimization, to enhance process efficiency. In order to achieve these goals, it is generally necessary to have the values of the variables or states involved in these calculations. There are many cases in which acceptable performance can be achieved by using only those variables that are accessible to measurement. However, in some complex systems, it is not possible to achieve optimum performance by using only the variables that can be measured.

During the 1960s, observers were introduced as an attempt to estimate the values of unmeasured variables. Luenberger, OBSERVING THE STATE OF A LINEAR SYSTEM, IEEE Trans. on Military Electronics, Vol. MIL-8, April 1964, p.74–80. Several years before the introduction of the observers, R. E. Kalman and R. Bucy defined a state estimator that is optimum with respect to the process noise and observation noise. Kalman, et al., NEW RESULTS IN SYSTEMS FILTERING AND PREDICTION PROBLEMS, Trans., ASME, Vol. 82D, No. 1, March 1961, p. 95–108. This state estimator (now called Kalman filter) has the structure of a linear observer, so the Kalman filter is considered as an optimum observer.

Although observers are useful for estimating the states of linear systems, their main use is in estimating the state variables that cannot be measured but are needed for process control or optimization. Unfortunately, observers have one significant drawback: the need of a reliable model. The Kalman filter gained immense popularity in engineering problems provided that the dynamic models of the systems were available. The models used in these early applications are called fundamental models or first principle because they are based on physicochemical principles. While this limitation can be overcome in some applications, it represents an almost impossible requirement in many complex systems. An alternate route for building models of systems when fundamental models are not available is that of building a model from input-output experimental data, also known as system identification.

One of the latest tools used for estimating immeasurable variables is Neural Networks (NN). This technique has been demonstrated to produce good results in systems where no fundamental models are available, and where the interactions between the inputs and outputs are highly nonlinear. NN is an input-output model that also uses a set of process data for identification (training). Unlike statistical estimators, they estimate a function without a mathematical model of how outputs depend on inputs. They are model-free estimators. They "learn from experience" with numerical and, sometimes, linguistic sample data. Since NNs do not use a mathematical model of how a system's output depends on its input—since they behave as model-free estimators—the same neural-network architecture and dynamics can be applied to a wide variety of problems. The procedure of estimating an unmeasurable variable using an observer, Kalman filter, neural network or any other mathematical tool that can be implemented to give on-line estimates based on other measurements is known as software sensor.

In any combustion process, several of the gas species can be measured with on-line analyzers, while others cannot be easily measured. More specifically, in furnaces, a TDL is capable of measuring $O_2$, CO, $CO_2$ and moisture, but other important species such as $H_2$ cannot be measured. In the preferred embodiment, the TDL measurements are used as input to a software sensor to estimate the $H_2$ and the NO on-line.

The following provides a summary of the application of software sensors in the preferred embodiment. The first step for constructing an input-output based software sensor based, such as some Kalman filters and neural networks, is the recording of data usually from well-designed experiments. The design of an identification experiment includes the selection of the signals to measure, when to measure them, which signals to manipulate and how to manipulate them. It also includes some more practical aspects, such as data conditioning before and after sampling.

While several variables and data manipulation can be done in the computer, the experimental data can be changed only by a new experiment, which can be a costly and time-consuming procedure. Therefore, it is worthwhile to design the experiment in order to generate data that are sufficiently informative. The first questions to be answered are where and what to measure, which in this case depend on the application and the TDL set up design. The last question is how often to measure, which is the same as defining the sampling interval. As a rule of thumb, it is recommended to choose the sampling time T, less than 0.1 τ, where τ is the dominant time constant of the process. Kalman, et al., GENERAL SYNTHESIS PROCEDURE FOR COMPUTER CONTROL FOR SINGLE-LOOP AND MULTI-LOOP SYSTEMS, AIEE Tans. Vol. 77, Part 2, p. 602 (1958).

The choice of the input signals has a very critical influence on the observed data. The input signals determine the operating point of the system and which parts and modes of the system are excited during the experiment. The freedom to choose the input signals can vary significantly with the application. When the process is expected to be nonlinear, it is a reasonable advice to carry out the experiment around the nominal operating point of the plant.

Once the software sensor approach is understood, an experimental design is developed. The experiments have to be informative enough as they generate data that are likely to be used for the software sensor development. More specifically, the inputs have to be manipulated in such a way that the outputs are useful enough to build reliable software sensors.

Two different approaches can be used to gather the necessary information. One is by performing several experiments varying the inputs with step changes at different levels and recording the output until they reach steady state. The number of experiments depends on the number of inputs and levels for all the inputs. This approach leads to a relatively large number of experiments, particularly to capture the dynamic behavior of the system.

A different approach is to vary the inputs in a persistently exciting fashion. A signal is said to have a persistently exciting spectrum if the spectrum is greater than zero for all frequencies. This approach reduces the number of experiments and guarantees data more useful for dynamic modeling. However, its implementation can be cumbersome in some practical situations.

When the data have been collected from the identification experiments, they are not likely to be in shape for immediate use in identification algorithms. Measurement noise, outliers, and offsets are some of the typical deficiencies. Most of these imperfections can be eliminated by the application of off-line filters, and statistical analysis.

Once the experimental design is developed, the network structure is determined. A neural network-based software sensor can be described in general as:

$$y_k = \Sigma w_i S(u_{k-1}, u_{k-2}, \ldots, u_{k-3}) + I_k \quad (1)$$

where S is a nonlinear function that describes the neuron behavior as a function of the inputs $U_k$. The inputs can be at different time intervals as shown in Equation (1) and have multiple inputs as well. The output of the neural network $y_k$ results by adding the transformations by the neuron function multiplied by the proper weights, and adding the biases. Equation (1) represents a neural network with only one hidden layer of neurons. Several layers of hidden neurons can be utilized, and so the outputs from one layer become the inputs to the second layer. The most common transfer function S, is the sigmoid function defined as:

$$S = \frac{1}{1 + e^{-cx}} \quad (2)$$

There are many other types of transfer functions, such as radial basis functions and triangular basis functions. Each one has its own properties and is recommended depending on the individual case. When the network contains delays, the input to the network would normally be a sequence of input vectors that occur in a certain time order. This network is known to be dynamic and is the most appropriate for a software sensor, as the inputs and outputs are autocorrelated. Kosko, NEURAL NETWORKS AND FUZZY SYSTEMS, Prentice Hall (1992).

After the network structure is determined, the network is trained. Once the information from the experiments has been treated and the structure of the neural network has been defined, the software sensor is ready to "learn." Learning encodes information. A system learns a pattern if the system encodes the pattern in its structure. The system structure changes as the system learns the information. For the neural network, learning means finding the values of the weights, $W_i$ and biases, $I_k$, of the network in Equation (1). This procedure is also known as training.

The learning rule is applied to train the network to perform some particular task. Most software sensors use supervised training, where the learning rule is provided with a set of examples of proper network behavior. As the inputs are applied to the network, the network outputs are compared to the targets. The learning rule is then used to adjust the weights and biases of the network in order to move the network outputs closer to the targets.

One common method for training a neural network is backpropagation. The input and output vectors are used to train a network until it can approximate a function. Networks with biases, a sigmoid layer, and a linear output layer are capable of approximating any function with a finite number of discontinuities. Standard backpropagation is a gradient descent algorithm. The term backpropagation refers to the manner in which the gradient is computed for nonlinear multiplayer networks. Properly trained backpropagation algorithms tend to give reasonable answers when presented with inputs that they have never seen. Typically, a new input will lead to an output similar to the correct output for input vectors used in training that are similar to the new input being presented. This generalization property makes it possible to train a network on a representative set of input-target pairs and get good results without training the network on all possible input output pairs.

As an example to demonstrate the concept off-gas composition data taken with an extractive sampling system installed at the exhaust gap of an EAF is shown in FIG. 1. The data illustrate the dynamic nature of the process with large fluctuations in concentration over time for this single run. Here a run refers to the duration of time from the point of charging the furnace with scrap to tapping the melted steel. In addition to CO, $CO_2$ and $O_2$ species, measurements of $H_2$ were also monitored with the extractive sampling system. The CO, $CO_2$ and $O_2$ were used to construct the software sensor NN model from a set of only four runs. The model used sigmoid transfer function with back propagation training.

Figure 2:
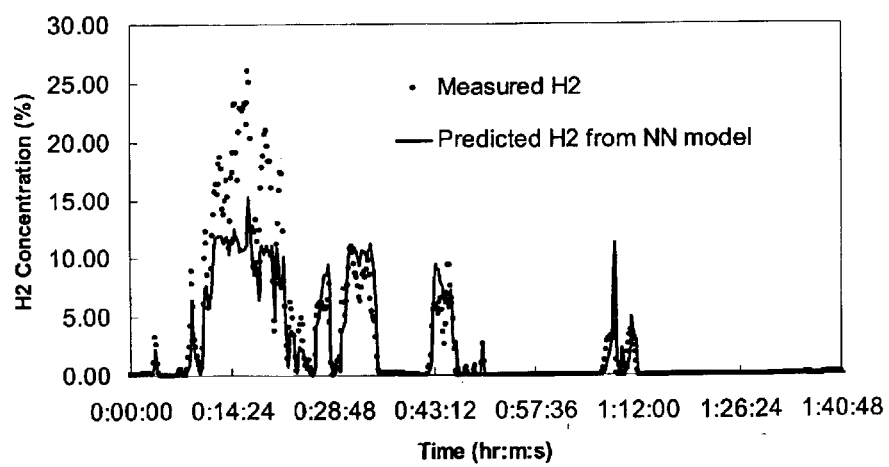
FIG. 2 shows data for predicting $H_2$ based on a species input data from FIG. 1.

Results of the model for predicting $H_2$ based on the species input data from FIG. 1 are shown in FIG. 2. With the limited set of data used in training the software sensor the overall trends in the $H_2$ are predicted. In some regions, the prediction is much better than others, but improved accuracy would be expected for a larger set of training data. Applying the software sensor with a diode laser measurement would also include the capability to monitor $H_2O$ concentration and gas temperature, which was not detected in extractive sampling measurements. The addition of $H_2O$ and gas temperature as model inputs should improve the accuracy in predicting $H_2$.

Figure 3:
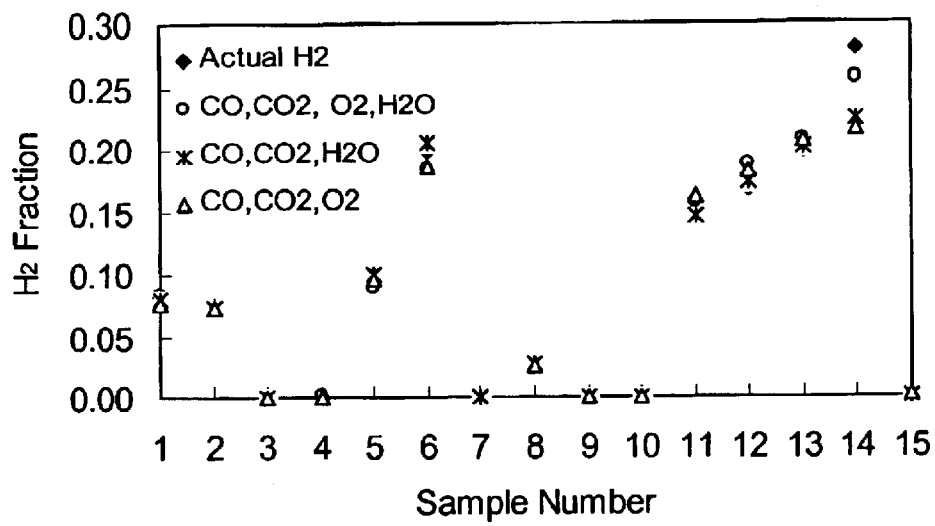
FIG. 3 shows data for predicting $H_2$ concentration using an NN model.
Figure 4:
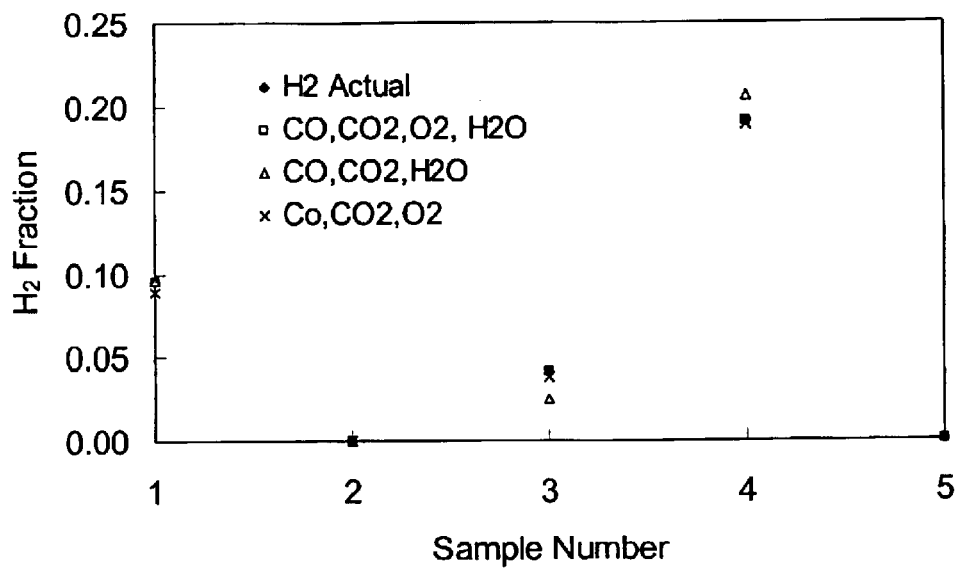
FIG. 4 shows data for predicting $H_2$ concentration using an NN model.

As an independent test for the NN to predict $H_2$ based on the target species CO, $CO_2$, $H_2O$, and $O_2$ as possible inputs (since all of these species can be monitored in the near-IR), a set of random data was constructed. In this case, the CO, $CO_2$, $H_2O$ and $O_2$ random mole fraction data was used in a constant T and P equilibrium model to calculate the species distribution at 1200 K. The NN model was constructed using different combinations of the target species to predict the $H_2$ fraction. Results from the NN model shown in FIG. 3 indicate that the NN model can predict $H_2$ from the various input combinations. However, the results in FIG. 4 represent the same set of data used in training the model. Therefore, a second set of random data was created to test the NN model created from the first set. These results are shown in FIG. 4, which again confirms the NN models capability in predicting $H_2$ from the various target species input combinations.

The link between the target species and $H_2$ results from the water-gas reaction

$$CO + H_2O \leftrightarrow CO_2 + H_2 \quad (3)$$

The rate of this reaction governs the $CO/CO_2$ and $H_2O/H_2$ ratios in the exhaust of all combustion processes. In particular, for fuel-rich combustion, as experienced on the EAF process at different times throughout the melting cycle, the resulting distribution of the species in reaction (3) is dependent on the temperature. Near about 1100 K, reaction (3) is uniformly equilibrated, i.e., $K_{eq} \rightarrow 1$. At temperatures less than about 1100 K, the product distribution favors CO and $H_2O$. In a well characterized process where equilibration is reached, $H_2$ could be determined directly from knowing the target species CO, $H_2O$ and $CO_2$ along with the gas temperature, as the $H_2$ concentration could be determined from the equilibrium constant of reaction (3).

Figure 5:
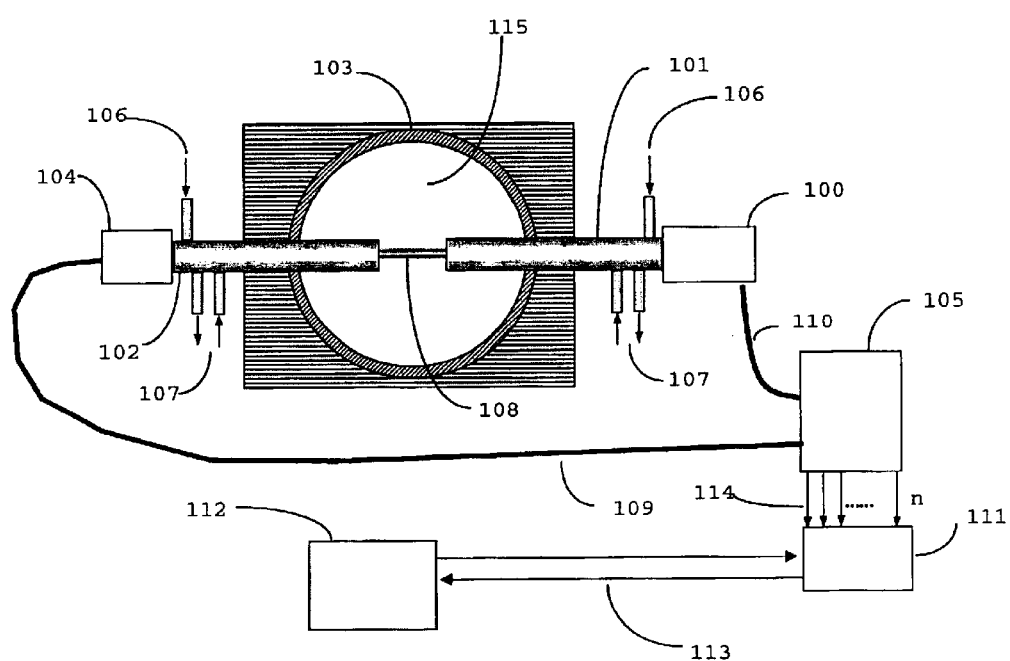
FIG. 5 is a schematic illustration of an first preferred embodiment of an apparatus for gas species monitoring.

An example of coupling the software sensor to a diode laser measurement system is shown in FIG. 5 for an EAF application. The basic measurement principle for conducting laser absorption measurements has been previously described in detail, Von Drasek, et al., MULTI-FUNCTIONAL INDUSTRIAL COMBUSTION PROCESS MONITORING WITH TUNABLE DIODE LASERS, Proceedings of SPIE, Vol. 4201 (2000), and only the main components of implementing a system are described here. The absorption measurement is conducted by launching a beam from a launch module 104 that houses optic components to shape the beam to the desired geometry. The beam is then transported through a water-cooled shielding pipe 102 and intersects the process gas as the beam 108 exits the pipe. The beam is received by shield pipe 101 and transported to the detector module 100 that houses the detection system. As shown, the system is mounted on the water-cooled EAF exhaust 103 with furnace exhaust gas flowing through volume 115. Water-cooling is provided to the shields at 107 and gas purge is introduced at 106 to maintain a positive pressure and to prevent particulate build up. The absorption signal from the module 100 is directed by fiber optic or twin-axial cable 110 to unit 105, which houses the lasers, associated electronics, and data acquisition system. From unit 105, the laser radiation is transported to the launch module by fiber optic cable 109, thus allowing the sensitive electronic components to be placed in a well-controlled environment.

The absorption measurements are processed by unit 105 to concentration units and the resulting values 114 can be sent to software sensor 111. The software sensor can be internal or external to unit 105. The predicted species concentration values can then be sent via data transmitter 113 to the process supervision system 112 for monitoring or control application. In addition, the process supervision system can also supply the software sensor with additional information to use in combination with the measured values to predict the targeted process parameter.

In addition to $H_2$ detection, extension to other gas species such as $NO_x$ or $SO_x$ can be predicted if the suitable input data to the NN model is available. As in the case of $H_2$, these species are also governed by gas composition and temperature.

Figure 6:
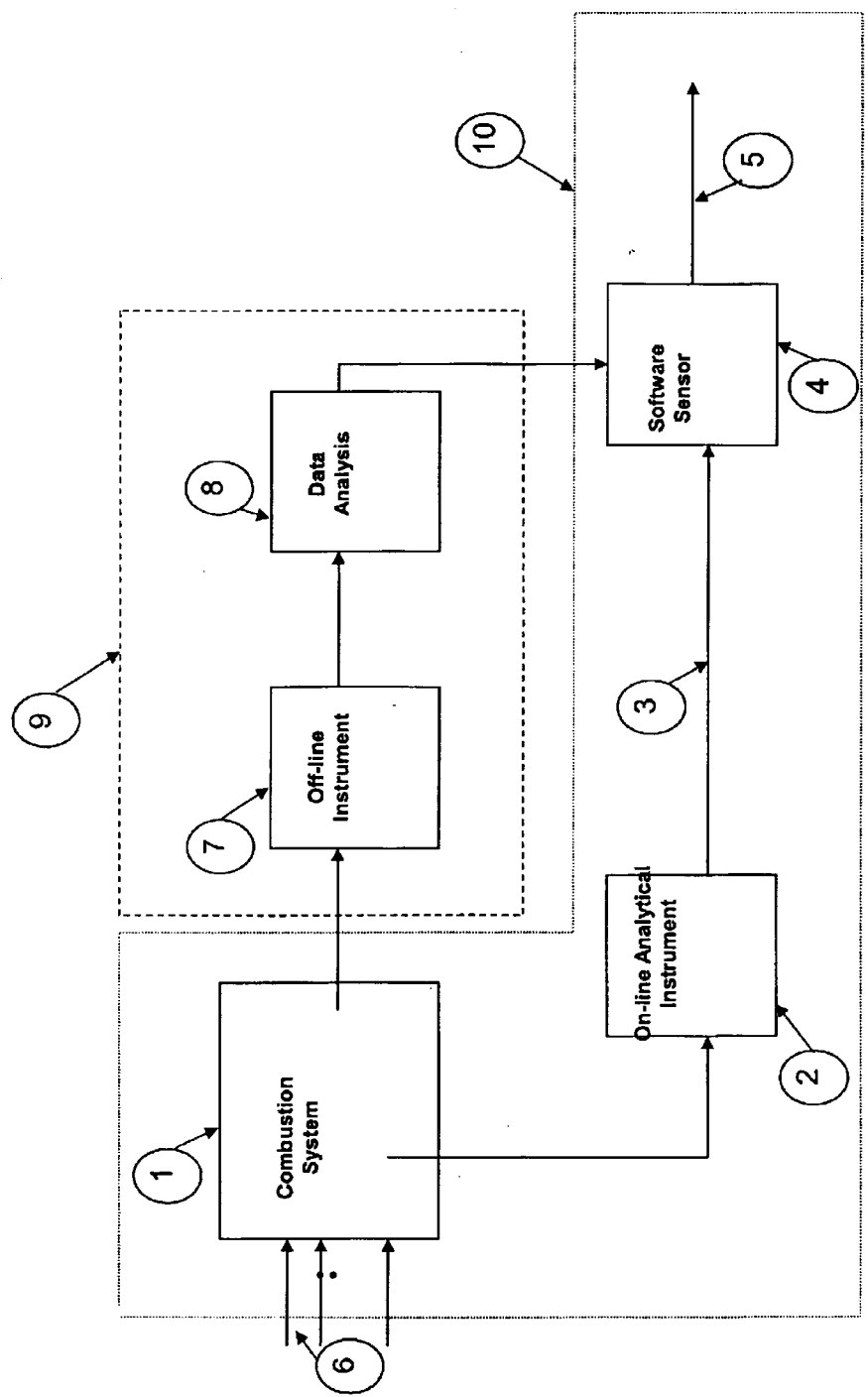
FIG. 6 illustrates a flowchart of the software sensor development.

Referring now to FIG. 6, the general logic to be employed in an apparatus 10 for using the method in developing the software sensor application is illustrated. As shown at 1, the combustion process from which gases to be measured is shown. The on-line analytical system 2 is preferably non-intrusive and provides a fast response. A set of gas species X, measured by an on-line analytical instrument is located at 3. The software sensor 4 relies on measurements of X and predicts measurements of Y after being trained.

A set 5 of on-line available measurements of X, plus on-line estimation of additional measurements of Y, provides the process inputs 6 that can be used to generate more quality information or data. An off-line instrument 7 can be used, if necessary, during training to collect off-line measurements of Y. Data analysis 8 of the process verifies the quality of data using correlation analysis, filtering, and data discrimination. The training procedure 9 thus "trains" the software sensor.

Thus, a method for indirect gas species monitoring based on measurements of selected gas species using optical absorption techniques is disclosed. Application of in situ absorption measurements of key combustion species such as $O_2$, CO, $CO_2$ and $H_2O$ can be used for process control and optimization. In situ absorption measurements offer a number of advantages over conventional extractive sampling in terms of maintenance and response time. However, the gas species accessible by near or mid-IR techniques are limited to species that absorb in this spectral region. Additionally, the absorption strength must be strong enough for the required sensitivity and isolated from neighboring absorption transitions. By coupling the gas measurement with a software sensor gas, species not accessible from the near or mid-IR absorption measurement can be predicted.

A method for indirect gas species monitoring for monitoring a gas sample of a combustion process for burning a combustible comprising is disclosed. An on-line, analytical technique to measure gas species in the sample of a combustion process is used. The gas species is selected from species that are detectable by the on-line, analytical technique and that correlate to at least one process parameter to be predicted. A software sensor is developed to correlate the gas species measurement with a process parameter to be predicted, resulting in a predicted result for the process parameter to be predicted.

One specific embodiment of the foregoing technique is described as follows. First, a sample of the gas from a combustion process to be measured is obtained. The sample contains at least one compound selected from the group consisting of $O_2$, CO, $CO_2$ and $H_2O$. A beam is launched from a launch module housing optic components constructed and arranged to shape the beam to a desired geometry, and the beam is shaped to the desired geometry. The beam is then transported through a first shielding pipe and is intersected with the sample as the beam exits the first shielding pipe. The beam is received within a second shielding pipe and transported to a detector module housing a detection system.

An absorption signal is generated from the module and directed to an optical unit housing a data acquisition system. The process data is analyzed using manipulated inputs to obtain desired outputs to generate data for software sensor development. If necessary, the $H_2$ level present is measured using a temporary measuring technique so that the compatibility of the initial correlation between the measured gas species data and measured $H_2$ data can be verified. Off-line filters and statistical analyses are employed as necessary to reduce measurement noise, outliers and offsets from the data. A neural-network based software sensor is then developed, and the network structure is determined.

The neural network is trained, by determining the values of the weights and biases of the network and coupling the gas species measurement with the software sensor to predict the $H_2$ level present. The ratio of $O_2$ to the combustible can then be adjusted to better achieve a stoichiometric balance.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for indirect gas species monitoring for monitoring a gas sample of a combustion process for burning a combustible comprising, in combination:
   using an on-line, analytical technique to measure gas species in the sample of a combustion process, the gas species being selected from species that are detectable by the on-line, analytical technique and that correlate to at least one process parameter to be predicted;
   developing the software sensor by analyzing process data using manipulated inputs to obtain desired outputs to generate data for software sensor development;
   verifying the compatibility of the initial correlation;
   applying off-line filters and statistical analyses as necessary to reduce measurement noise, outliers and offsets from the data;
   determining a neural-network based software sensor;
   determining the network structure;
   training the neural network by determining the values of the weights and biases of the network; and
   coupling the gas species measurement with the software sensor to predict the process parameter to be predicted.

2. The method described in claim 1, further comprising adjusting the ratio of $O_2$ to the combustible to better achieve a stoichiometric balance.

3. The method described in claim 1, wherein the on-line analytical technique comprises optical absorption techniques.

4. The method described in claim 3, wherein the optical absorption technique comprises a diode laser.

5. A method for indirect gas species monitoring for monitoring a gas sample of a combustion process for burning a combustible comprising, in combination:
   using optical absorption techniques to measure gas species in the sample of a combustion process, the gas species being selected from the group consisting of $O_2$, CO, $CO_2$ and $H_2O$;
   analyzing process data using manipulated inputs to obtain desired outputs to generate data for software sensor development;
   measuring the $H_2$ level present using a temporary measuring technique;
   verifying the compatibility of the initial correlation between the measured gas species data and measured $H_2$ data;
   applying off-line filters and statistical analyses as necessary to reduce measurement noise, outliers and offsets from the data;
   determining a neural-network based software sensor;
   determining the network structure;
   training the neural network by determining the values of the weights and biases of the network;
   coupling the gas species measurement with the software sensor to predict the $H_2$ level present.

6. The method described in claim 5, further comprising adjusting the ratio of $O_2$ to the combustible to better achieve a stoichiometric balance.

7. A method for indirect gas species monitoring for monitoring an off-gas of a combustion process for burning a combustible comprising, in combination:
   obtaining an off-gas sample of a combustion process to be monitored, the off-gas sample containing at least one compound selected from the group consisting of $O_2$, CO, $CO_2$ and $H_2O$;
   launching a beam from a launch module housing optic components constructed and arranged to shape the beam to a desired geometry;
   shaping the beam to a desired geometry;
   transporting the beam through a first shielding pipe and intersecting the beam with the off-gas sample as the beam exits the first shielding pipe;
   receiving the beam with a second shielding pipe and transporting it to a detector module housing a detection system;
   generating an absorption signal from the module;
   directing the absorption signal to an optical unit housing a data acquisition system;
   developing a software sensor; and
   coupling the gas species measurement with the software sensor to predict the $H_2$ level present.

8. A method for indirect gas species monitoring for monitoring an off-gas of a combustion process for burning a combustible comprising, in combination:
   obtaining an off-gas sample of a combustion process to be monitored, the off-gas sample containing at least one compound selected from the group consisting of $O_2$, CO, $CO_2$ and $H_2O$;
   launching a beam from a launch module housing optic components constructed and arranged to shape the beam to a desired geometry;
   shaping the beam to a desired geometry;
   transporting the beam through a first shielding pipe and intersecting the beam with the off-gas sample as the beam exits the first shielding pipe;
   receiving the beam with a second shielding pipe and transporting it to a detector module housing a detection system;
   generating an absorption signal from the module;
   directing the absorption signal to an optical unit housing a data acquisition system;
   analyzing process data using manipulated inputs to obtain desired outputs to generate data for software sensor development;
   measuring the $H_2$ level present using a temporary measuring technique;
   verifying the compatibility of the initial correlation between the measured gas species data and measured $H_2$ data;
   applying off-line filters and statistical analyses as necessary to reduce measurement noise, outliers and offsets from the data;
   determining a neural-network based software sensor;
   determining the network structure;
   training the neural network by determining the values of the weights and biases of the network; and
   coupling the gas species measurement with the software sensor to predict the $H_2$ level present.

9. The method described in claim 8, further comprising adjusting the ratio of $O_2$ to the combustible to better achieve a stoichiometric balance.

10. The method described in claim 5, wherein the optical absorption technique comprises a diode laser.

11. A method for indirect gas species monitoring for monitoring a gas sample of a combustion process for burning a combustible comprising, in combination:

using optical absorption techniques to measure gas species in the sample of a combustion process, the gas species being selected from the group consisting of $O_2$, CO, $CO_2$ and $H_2O$;

analyzing process data using manipulated inputs to obtain desired outputs to generate data for software sensor development;

measuring a level present of a further gas species selected from the group consisting of NO, NOx, and SOx using a temporary measuring technique;

verifying the compatibility of the correlation between the measured gas species data and the level present of the further gas species;

applying off-line filters and statistical analyses as necessary to reduce measurement noise, outliers and offsets from the data;

determining a neural-network based software sensor;

determining the network structure;

training the neural network by determining the values of the weights and biases of the network; and coupling the gas species measurement with the software sensor to predict the level of the further gas species present.

12. The method described in claim 11, further comprising adjusting the ratio of $O_2$ to the combustible to better achieve a stoichiometric balance.

* * * * *

UNITED STATES PATENT AND TRADEMARK OFFICE
CERTIFICATE OF CORRECTION

PATENT NO.       : 6,859,766 B2
APPLICATION NO.  : 10/364675
DATED            : February 22, 2005
INVENTOR(S)      : William A. Von Drasek and Victor M. Saucedo It is certified that error appears in the above-identified patent and that said Letters Patent is hereby corrected as shown below:

Insert as new paragraph [0001]:  --This invention was made with government support under Contract No. DE-FC36-00CH11030 awarded by the Department of Energy. The government has certain rights in this invention.--

Signed and Sealed this

First Day of August, 2006

JON W. DUDAS
*Director of the United States Patent and Trademark Office*